US007959859B2

(12) United States Patent
Sparks et al.

(10) Patent No.: US 7,959,859 B2
(45) Date of Patent: Jun. 14, 2011

(54) ULTRASONIC SANITATION DEVICE AND ASSOCIATED METHODS

(76) Inventors: David W. Sparks, Thonotosassa, FL (US); Roy Beckett, Orlando, FL (US)

( * ) Notice: Subject to any disclaimer, the term of this patent is extended or adjusted under 35 U.S.C. 154(b) by 866 days.

(21) Appl. No.: 11/624,317

(22) Filed: Jan. 18, 2007

(65) Prior Publication Data

US 2007/0224080 A1 Sep. 27, 2007

Related U.S. Application Data

(63) Continuation-in-part of application No. 11/277,176, filed on Mar. 22, 2006.

(51) Int. Cl.
*A61L 2/00* (2006.01)
*A61L 2/18* (2006.01)
*A61L 9/00* (2006.01)
*B01J 7/00* (2006.01)

(52) U.S. Cl. ............. 422/28; 422/20; 422/292; 422/306

(58) Field of Classification Search .................... 422/20, 422/128, 28; 433/86; 505/401; 128/200.16; 261/81, DIG. 48
See application file for complete search history.

(56) References Cited

U.S. PATENT DOCUMENTS 1,929,234 A * 10/1933 Anderson ....................... 261/54
3,559,427 A 2/1971 Baker
3,561,444 A * 2/1971 Boucher .................. 128/200.16
3,729,138 A 4/1973 Tysk
3,828,773 A * 8/1974 Buch et al. ............... 128/200.16
4,137,258 A * 1/1979 Moore et al. .................. 562/477
4,366,125 A 12/1982 Kodera et al.
4,385,911 A 5/1983 Popeil et al.
4,410,139 A * 10/1983 Nishikawa et al. ........ 239/102.2
4,517,159 A 5/1985 Karlson
4,731,204 A * 3/1988 Noma et al. .................... 261/30
5,017,199 A 5/1991 Etchepare
5,300,260 A * 4/1994 Keshet et al. .................. 261/81

(Continued)

FOREIGN PATENT DOCUMENTS

JP 58-72000 4/1983

(Continued)

OTHER PUBLICATIONS
U.S. Appl. No. 60/600,252.*
(Continued)

*Primary Examiner* — Sean Conley
*Assistant Examiner* — Regina Yoo
(74) *Attorney, Agent, or Firm* — Allen Dyer Doppelt Milbrath & Gilchrist, P.A.

(57) ABSTRACT

A device for sanitizing a space includes a tank having an interior space for holding an aqueous sanitizing liquid, the tank having a bottom sector, a front sector having a rear wall, and a rear sector having a front wall, the rear sector front wall and the front sector rear wall forming a substantially "V"-shaped air pathway within the interior space. A reactor vessel is positioned within the bottom sector of the tank, a top edge of the reactor vessel in spaced relation from a notch in the "V"-shaped air pathway. A vibratable ultrasonic head array is positionable within and beneath a top edge of the reactor vessel and is submergable within the reactor vessel for vibrating the disc to form an atomized fog of particles from the liquid. Air can be drawn into the air inlet, and the formed atomized fog can be exhausted from the exhaust outlet.

10 Claims, 11 Drawing Sheets

U.S. PATENT DOCUMENTS

| | | | |
|---|---|---|---|
| 5,611,967 A | | 3/1997 | Jane et al. |
| 5,645,769 A | * | 7/1997 | Tamaru et al. ................. 261/30 |
| 5,653,919 A | * | 8/1997 | White et al. .................... 261/21 |
| 5,783,117 A | | 7/1998 | Byassee et al. |
| 5,868,999 A | | 2/1999 | Karlson |
| 6,102,992 A | * | 8/2000 | Berg et al. ...................... 96/361 |
| 6,244,576 B1 | * | 6/2001 | Tsai .............................. 261/141 |
| 6,245,361 B1 | | 6/2001 | Merritt |
| 6,379,616 B1 | | 4/2002 | Sheiman |
| 6,379,633 B1 | | 4/2002 | Garlick |
| 6,537,494 B2 | | 3/2003 | Garlick |
| 6,589,481 B1 | | 7/2003 | Lin et al. |
| 6,682,606 B2 | * | 1/2004 | Walker .............................. 134/6 |
| 6,685,895 B1 | | 2/2004 | Lin |
| 7,145,052 B1 | * | 12/2006 | Watkins ........................ 588/320 |
| 7,524,454 B1 | * | 4/2009 | Sparks ............................ 422/20 |
| 2003/0042629 A1 | * | 3/2003 | Eom .............................. 261/81 |
| 2003/0127535 A1 | * | 7/2003 | Adiga et al. ............... 239/102.1 |
| 2003/0127753 A1 | | 7/2003 | Bachert |
| 2003/0143110 A1 | | 7/2003 | Kritzler et al. |
| 2004/0005240 A1 | | 1/2004 | Adiga et al. |
| 2004/0009094 A1 | | 1/2004 | Adiga et al. |
| 2004/0022673 A1 | | 2/2004 | Protic |
| 2004/0057866 A1 | | 3/2004 | Zumeris et al. |
| 2004/0146425 A1 | | 7/2004 | Joshi |
| 2005/0031486 A1 | | 2/2005 | Mole et al. |
| 2005/0074359 A1 | * | 4/2005 | Krieger et al. ................... 422/28 |
| 2005/0212152 A1 | * | 9/2005 | Reens .............................. 261/81 |
| 2005/0214386 A1 | * | 9/2005 | Shaheen et al. ............... 424/661 |
| 2005/0220665 A1 | | 10/2005 | Ding |
| 2006/0213508 A1 | * | 9/2006 | Murray et al. ........... 128/200.16 |
| 2006/0216214 A1 | * | 9/2006 | Brown et al. ................. 422/124 |
| 2006/0289490 A1 | * | 12/2006 | Mielnik ........................ 219/628 |
| 2007/0193132 A1 | * | 8/2007 | Roscioli ....................... 52/169.6 |
| 2008/0193650 A1 | * | 8/2008 | Lyon ............................. 427/299 |

FOREIGN PATENT DOCUMENTS

| | | |
|---|---|---|
| JP | 08313019 A * | 11/1996 |
| JP | 11-123357 | 5/1999 |
| JP | 2003-214664 | 7/2003 |

OTHER PUBLICATIONS

U.S. Appl. No. 60/694,513.*

English machine translation of JP 08-313019.*

* cited by examiner

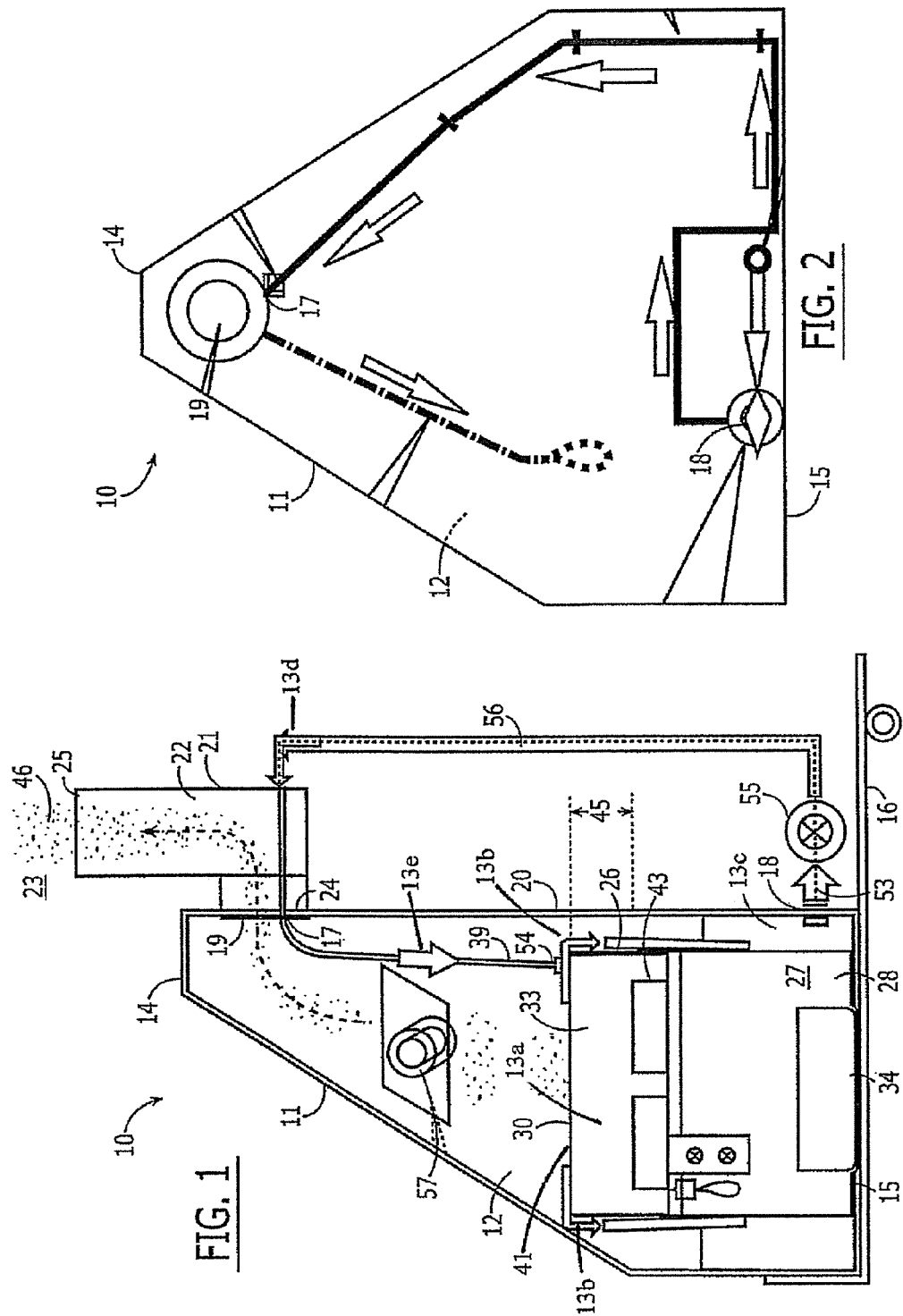

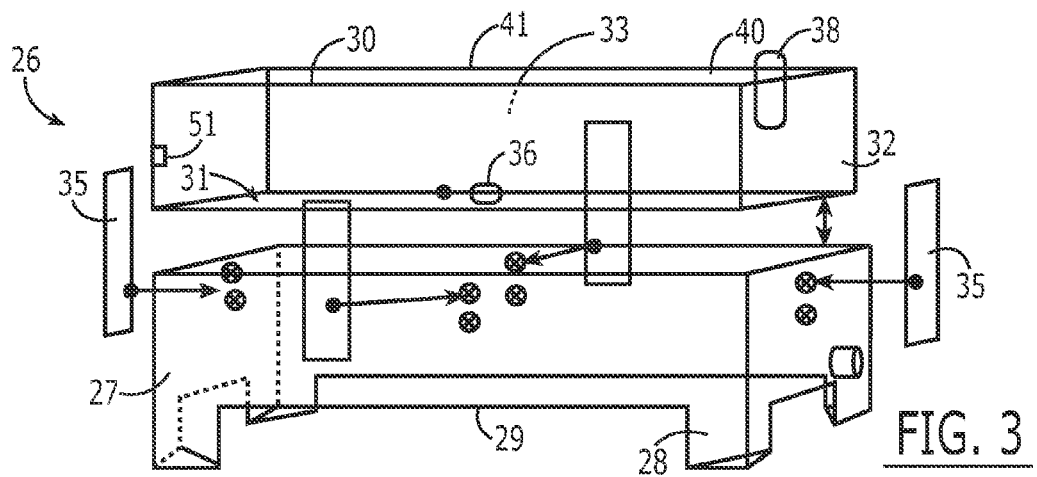
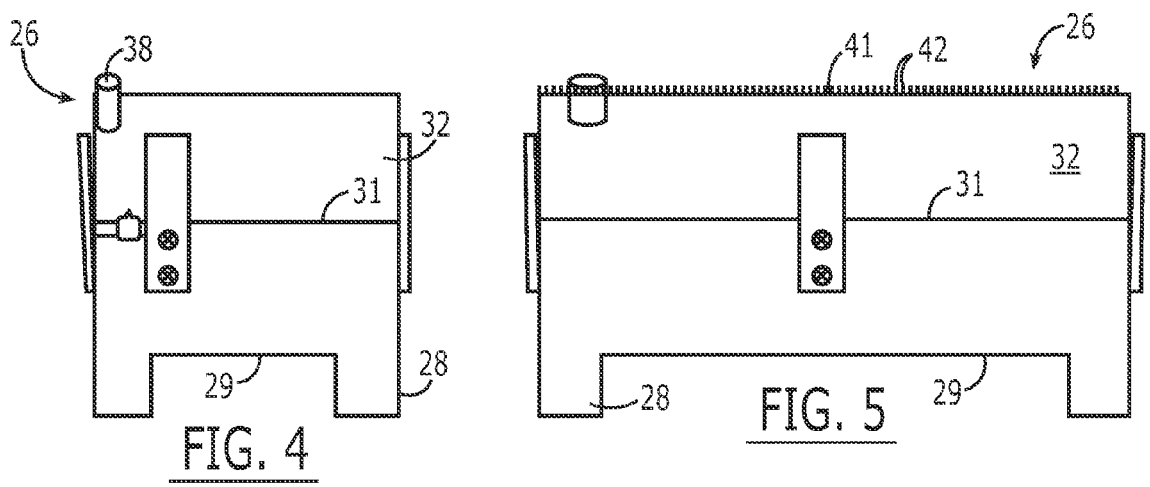
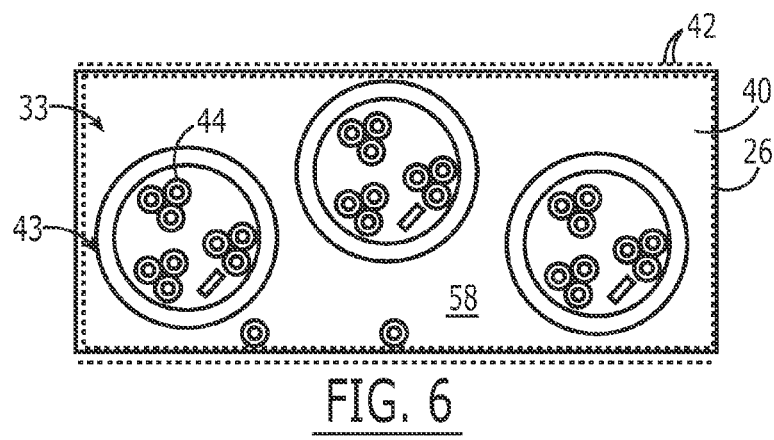

ULTRASONIC SANITATION DEVICE AND ASSOCIATED METHODS

CROSS-REFERENCE TO RELATED APPLICATION

This application is a continuation-in-part of co-pending application Ser. No. 11/277,176, filed Mar. 22, 2006, entitled "Ultrasonic Sanitation Device and Associated Methods."

BACKGROUND OF THE INVENTION

1. Field of the Invention

The present invention relates to systems and methods for sanitizing enclosed spaces, and, more particularly, to such systems and methods that are capable of treating spaces three-dimensionally.

2. Description of Related Art

The sanitization and disinfection of enclosed spaces has become an issue of increasing importance owing to the possible presence of both natural and deliberately introduced contaminants. Since most commercial buildings are "sealed," that is, their windows cannot be opened, circulation of "fresh" air is typically not possible within a particular room. Similarly, most houses are now effectively sealed, with mostly processed air being circulated. In addition, some forms of conveyance, especially airplanes, are of necessity sealed against the environment during flight.

The enclosed nature of modern spaces has led to such problems as "sick building syndrome," since molds and mildews can flourish in enclosed, damp environments, and also to the possibility of the natural or deliberate introduction of more insidious threats to life, such as biological and chemical agents. Some infectious agents, such as hepatitis virus and staph bacteria such as MRSA, are known to survive in areas such as hospitals and other healthcare facilities, and there, as well as in other places such as cruise ships, pose a health threat.

Another area of concern is the interior of vehicles, such as emergency vehicles. Such vehicles can include ambulances, fire rescue units, police cars, and other EMS vehicles. In addition, other publicly used vehicles such as buses, boats, subway cars, trains, and taxis can be of concern. These vehicles are seldom, if ever, cleaned to a level sufficient to ensure the eradication of infectious agents.

At present most sanitizing and disinfecting agents are "two-dimensional," that is, they are applied to accessible surfaces. For example, when cleaning a table, typically the cleanser is applied to the table top, but not the underside.

"Fogging" agents are known for eradicating pests such as fleas and other insects. Ionization-type purifiers are also known in the art that use electrostatic means to collect allergens and pollutants.

Therefore, it would be beneficial to provide a more effective device, system, and method for sanitizing enclosed spaces in a three-dimensional fashion.

SUMMARY OF THE INVENTION

The present invention provides a device for sanitizing a space. The device comprises a tank having an interior space for holding an aqueous sanitizing liquid. A reactor vessel is supported within the interior space and above a bottom of the tank. Means are provided for maintaining a liquid depth in the tank interior space to a level beneath a top edge of the reactor vessel. An ultrasonic head array comprising an ultrasonically vibratable disc for generating ultrasonic energy is positionable within and beneath the top edge of the reactor vessel. Means are included for transferring liquid from the tank interior space to the reactor vessel to a level for substantially submerging the ultrasonic head array. Means are also provided for vibrating the disc to form an atomized fog of particles from the aqueous sanitizing liquid. Further means are provided for exhausting the formed atomized fog from the reactor vessel to a space exterior of the tank.

The device may also be used to distribute a liquid by creating the atomized fog as above and directing the fog to a desired location, for example, for delivering fertilizer or pesticide to a plot of land, for watering plants, or for distributing a skin-care product to the skin of a user, although these uses are not intended to be limiting.

The device of the present invention is able to reach all areas in a space where air can penetrate, and, since the atomized particles have been found to remain airborne longer than conventional mists, treatment is more thorough, and less chemical is required than used by previously known devices. A typical room of dimensions 12×12×10 ft can be disinfected and re-occupied in 20 min or less, for example.

An alternate embodiment of the device of the present invention is configured for use in sanitizing the interior of a vehicle. This embodiment includes a hose having a proximal end affixable in fluid communication with the exhaust outlet. Means for sealing an at least partially open access area of a vehicle is provided, wherein the sealing means has an aperture in fluid communication with a distal end of the hose. This embodiment of the invention is useful for enabling a sanitizing treatment of the vehicle's interior.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 is a side cross-sectional view of an embodiment of the sanitizing device of the present invention.

FIG. 2 is a rear view of the device of FIG. 1.

FIG. 3 is an exploded perspective view of the reactor tray of the device of FIG. 1.

FIG. 4 is a side view of the reactor tray.

FIG. 5 is a rear view of the reactor tray.

FIG. 6 is a top view of the reactor tray with ultrasonic head arrays positioned therein.

FIG. 7 is a side-top perspective view of an ultrasonic reactor head array, with one disk seen in exploded view.

FIG. 8 is an exploded view of a reactor head array disk.

FIG. 9 is a side perspective view of an alternate embodiment of an exhaust system including a diverter element.

FIG. 10 is a side cross-sectional view of an alternate embodiment incorporating a heating exhaust.

FIGS. 11A-11D are side cross-sectional views of different exemplary embodiments of the reactor tray.

FIG. 12 is a schematic illustration of a side view of an alternate embodiment of the device.

FIG. 13 is a top/side perspective view of the inside of a reactor vessel for the embodiment of FIG. 12.

FIG. 14 is a side cross-sectional view of an inner tank.

DETAILED DESCRIPTION OF THE PREFERRED EMBODIMENTS

Figure 7:
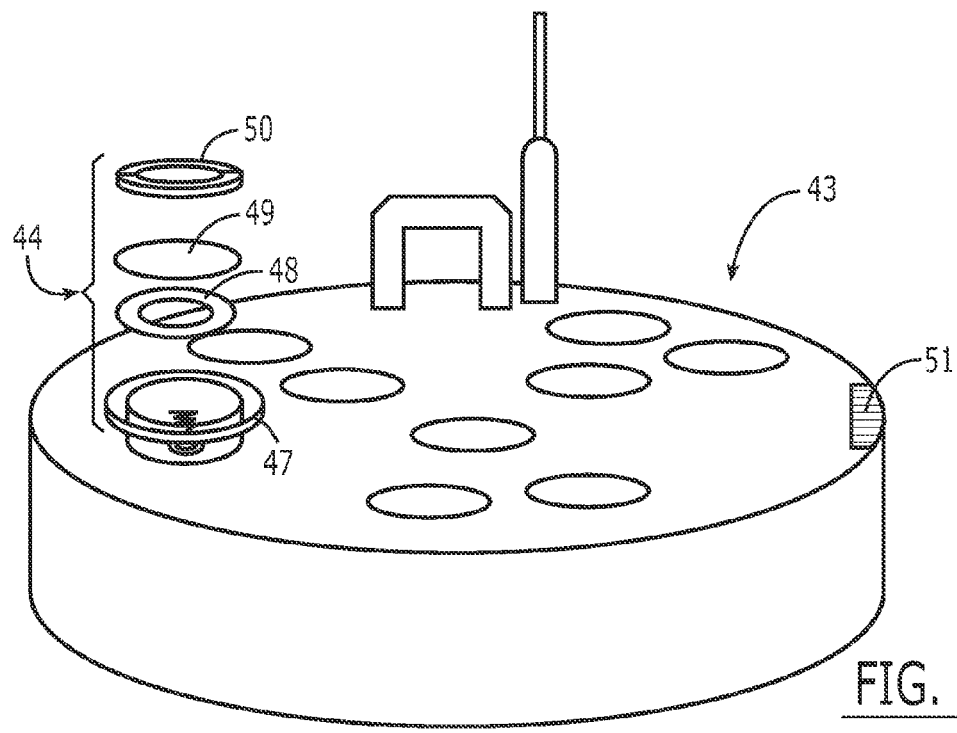

A description of the preferred embodiments of the present invention will now be presented with reference to FIGS. 1-26. The device 10 in a first embodiment for sanitizing a space includes a tank 11 (FIGS. 1 and 2) that has an interior space 12 for holding an aqueous sanitizing liquid 13. In a particular embodiment, the tank's top end 14 is substantially smaller than its bottom 15. Further, the tank 11 may be configured for placement upon a wheeled cart 16 for ease of transport.

The tank 11 has a liquid line aperture 17 adjacent the top 14 and a liquid outlet 18 adjacent the bottom 15. The tank 11 can comprise a material adapted to maintain a static charge, such as, but not intended to be limiting, a high-density polyethylene (HDPE) material.

A fog outlet 19 is positioned adjacent the tank's top 14 along the rear wall 20, and is in fluid communication with a chimney 21 having a bore 22 therethrough leading to a space 23 exterior of the tank 11. In a preferred embodiment, the chimney bore 22 has an elbow therein, shown by the dotted line in FIG. 1, meeting the fog outlet 19 at a first end 24 and the exterior space 23 at the second, upwardly directed end 25.

A reactor vessel 26 is supported within the tank's interior space 12 and above the tank's bottom 15. In a particular embodiment illustrated in FIGS. 3-5, not intended to be limiting, the reactor vessel 26 comprises a substantially hollow rectangular lower section 27 that has a plurality of support legs 28 that extend from a bottom 29 thereof. An upper substantially rectangular section 30 comprises a bottom 31 and four enclosing walls 32 that extending upwardly from the upper section's bottom 31 and are adapted to contain liquid in the interior space 33 formed thereby. The lower 27 and the upper 30 sections are affixable together with the upper section 30 atop the lower section 27 and are positionable within the tank's interior space 12 with the support legs 28 contacting the bottom surface 34 of the tank's interior space 12. One of skill in the art will recognize that additional embodiments for the reactor tray 26 could be envisioned, and that the shape presented here in is intended to be exemplary only.

In a particular embodiment, not intended to be limiting, the reactor vessel 26 is formed in two parts 27,30 in order to permit insertion into a particular tank 11. Here the parts 27,30 are held together with the use of joiner clips 35 that are screwed onto the lower section 27 and serve to brace the sections 27,30 together. The reactor vessel 26 has one or more drain holes 36 extending from the interior space 33 of the reactor vessel 26 through to the tank's interior space 12 and is positioned adjacent the bottom 31 of the reactor vessel's interior space 33.

The reactor vessel 26 further has affixed thereto a hose clamp 38 for supporting a liquid line 39, which will be discussed in the following. The top surface 40 of the upper section 30 should preferably have an area substantially greater than the top 14 of the tank 11.

Another feature of particular embodiments of the reactor vessel 26 is that the top edge 41 of the upper section 30 can have a plurality of notches 42 therealong. These notches 42 can assist in permitting liquid to pass therethrough, but to substantially prevent foam from passing therethrough, thus retaining foam within the upper section 30 and not permitting it into the return line 39.

Figure 8:
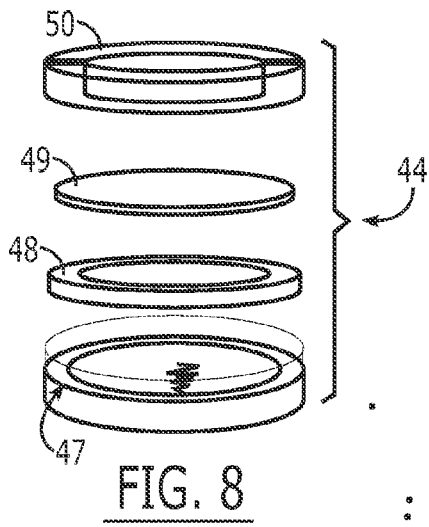

Positioned within the reactor vessel's upper section 30 is a plurality of ultrasonic head arrays 43, here, three ultrasonic head arrays (FIGS. 6-8). Each of the head arrays 43 comprises a plurality, here, nine, vibratable heads 44 for generating ultrasonic energy. The head arrays 43 are positioned so as to be submersible within the reactor vessel 26, the submersion depth 45 optimized for production of an atomized fog 46 of particles from the liquid 13 therewithin. Preferably the fog 46 comprises negatively charged particles, which aid dispersal and space coverage. It has been found that the depth 45 of the liquid column and also the vibration frequency affects the focus of the sound waves. The signal for activating the discs 44 is transmitted from devices known in the art, such as by way of a manual switch or level sensor.

The ultrasonic head arrays 43 believed at the time of filing to represent a best mode of carrying out the invention comprise head arrays obtained from Sonaer Ultrasonics (Farmingdale, N.Y.). An exemplary head array that can be used comprises part number T241, although this is not intended to be limiting. The fog 46 created by these head arrays 43 can contain particles in a range of 0.25-5.0 μm, although this is not intended to be limiting, as the size may be larger in some instances. Each of the discs 44 include a substantially toroidal O-ring seat 47, a Viton O-ring 48 seated on the O-ring seat 47, a ceramic disk 49 positioned atop the O-ring 48, and a substantially toroidal retaining ring 50 positioned in circumferentially retaining relation atop the ceramic disk 49. The discs 44 are known in the art to be supplied with silicone O-rings, but it has been found that the increased stiffness and chemical resistance of the Viton material is beneficial to the invention.

The drain hole 36 discussed above has been found to be beneficial in extending the life of the device 10 by keeping the head arrays 43 dry. A level sensor 51 can also be provided for automatically turning the head arrays 43 on and off depending upon the presence or absence of liquid. The level sensor 51 can be positioned either on the tank 11 or on the head arrays 43 themselves.

Means are included for transferring liquid from the tank's interior space 12 to the reactor vessel 26 to a level for substantially submerging the ultrasonic head array 43. For this purpose is provided a liquid line 39 that is in fluid communication with the tank's liquid outlet 18 at an inlet end 53 and with the reactor vessel 26 at an outlet end 54. The liquid line 39 in this embodiment passes through the liquid line aperture 17 between the inlet end 53 and the outlet end 54, and is affixed to the reactor vessel 26 with the use of the hose clamp 38.

As illustrated with reference again to FIG. 1, a pump 55 is provided along the liquid line 39 that is operable to move liquid 13 through the liquid line 39 from the tank's interior space 12 beneath the reactor vessel 26 to the interior space 33 of the reactor vessel 26. The liquid 13 is pumped from the bottom 15 of the tank 11 through the liquid line 39 via the clear portion 56 and into the tank through the liquid line aperture 17 near the top end 14 of the tank. The liquid line outlet end 54 delivers the liquid into the upper section 30 of the reactor vessel 26 allowing the upper section 30 to be filled with the liquid 13*a* and an overflow of liquid 13*b* (illustrated with arrows) to continuously cascade over the edge 41 into the bottom 15 of the tank 11 wherein the liquid 13*c* is pumped through the liquid outlet as the liquid 13*d* through the clear line portion 56 and to the liquid line aperture 17, and wherein the liquid 13*e* is delivered to the upper section 30 to repeat the cycle from liquid 13*a*. For one embodiment of the invention as herein described by way of example, the liquid line 39 comprises a substantially clear material, so that a portion 56 of the liquid line 39 exterior of the tank 11 can thereby serve as an indicator of a liquid level within the tank's interior space 12 when the pump 55 is not operating. The placement of the liquid line portion 56 outside the tank 11 has also proven beneficial in assisting in cooling the liquid upon its pathway to the reactor vessel 26. In addition, a filtration element may be added to eliminate contaminants along the liquid line 39.

The device 10 further includes means for exhausting the atomized fog 46 that is formed to an exterior of the tank 11. This can be accomplished, for example, with the use of a fan 57 positioned within the tank's interior space 12 above the reactor vessel 26 and positioned to direct the formed atomized fog 46 from a top surface 58 of liquid 13 in the reactor vessel 26 to the fog outlet 19.

An additional feature that may be provided in certain circumstances includes a means for heating the fog 46, which has been found to reduce the size of the fog particles. Such a heating means may comprise, for example, a coil 59 (FIG. 10) positioned along the exhaust path.

Figure 9:
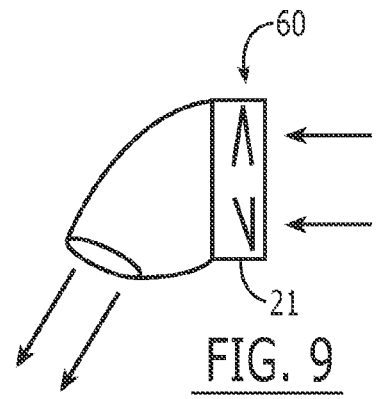
Figure 10:
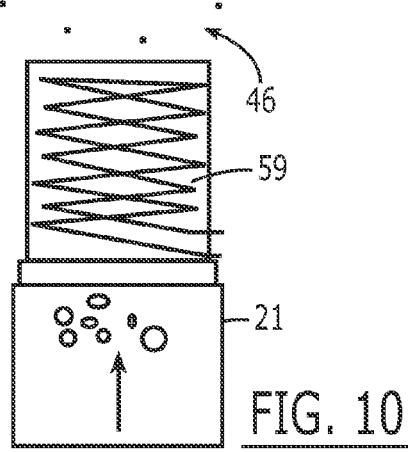

It will be understood by one of skill in the art that many variations on the embodiment discussed above may be contemplated. For example, the exhaust system may include a diverter element 60 as illustrated in FIG. 9.

Figure 11A:
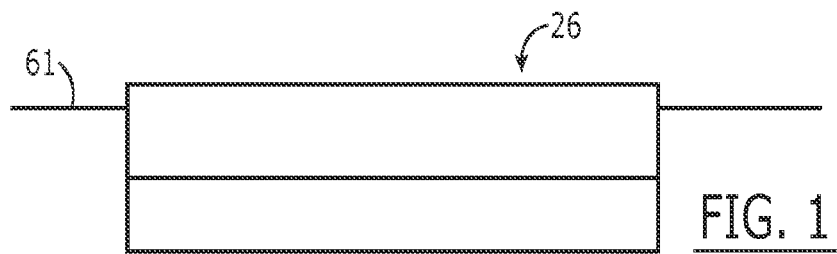
Figure 11B:
Figure 11C:
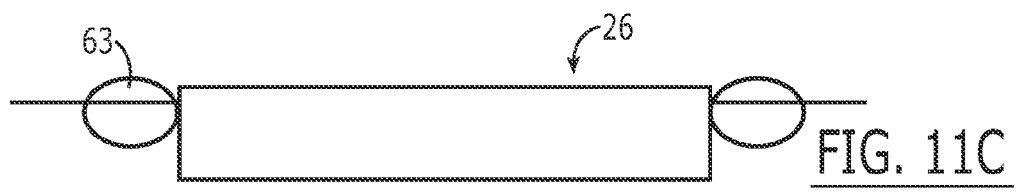
Figure 11D:
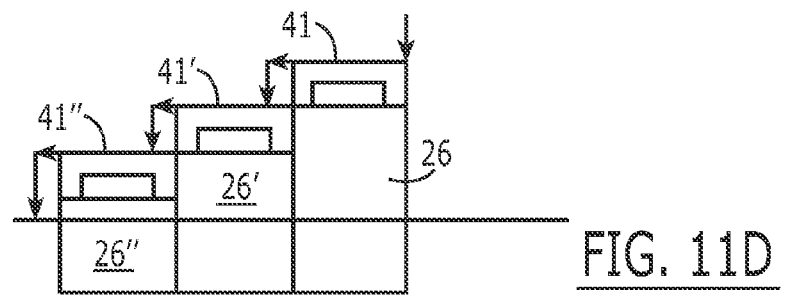
Figure 12:
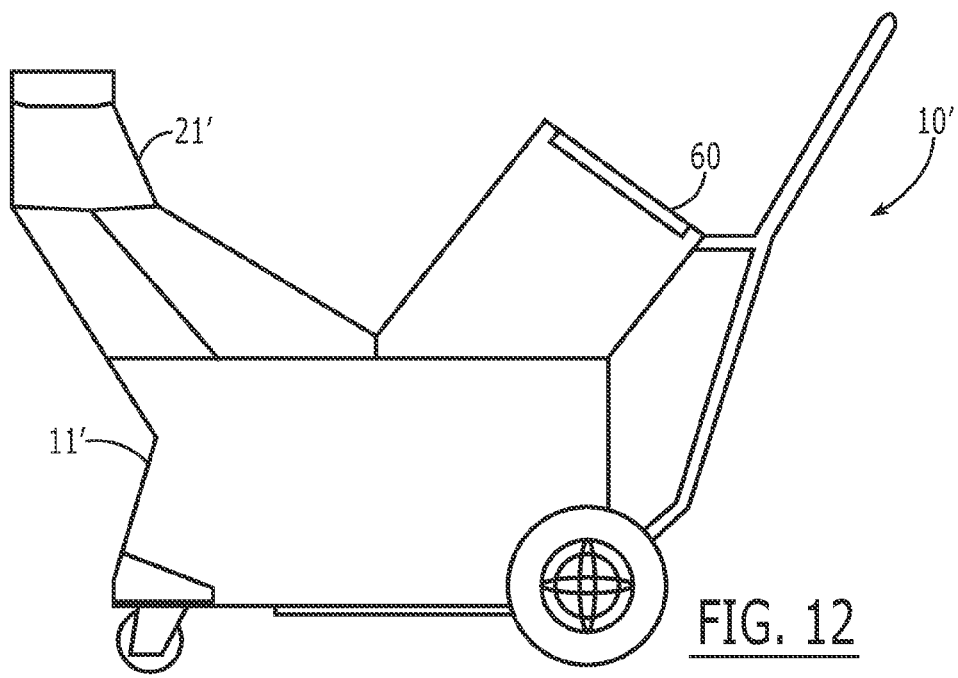

In addition, various alternate means may be employed to support the ultrasonic head arrays 43, as shown in the flotation elements of FIGS. 11A-11C, wherein a foam floater 61 (FIG. 11A), a sealed air cavity 62 (FIG. 11B), or a floater ring 63 (FIG. 11C) may be used to support the tray 26 and the head arrays 43.

Further, the reactor tray 26 may include a plurality of reactor vessels 26,26'26" positioned adjacent each other, the top edge 41 of a first reactor vessel 26 above the top edge 41' of a second reactor vessel 26', and so on. In this embodiment the liquid transferring means is adapted to transfer liquid 13 into the first reactor vessel 26, thereby permitting a cascade of liquid from the first reactor vessel 26 into the second reactor vessel 26' and thence into the third reactor vessel 26" during operation.

The shape of the device as illustrated herein is not intended to be limiting. For example, in an alternate embodiment 10' shown in FIG. 12, the tank 11' may have a chimney 21' at the front of the tank, with a liquid inlet 60 toward the rear of the tank 11'.

Figure 13:
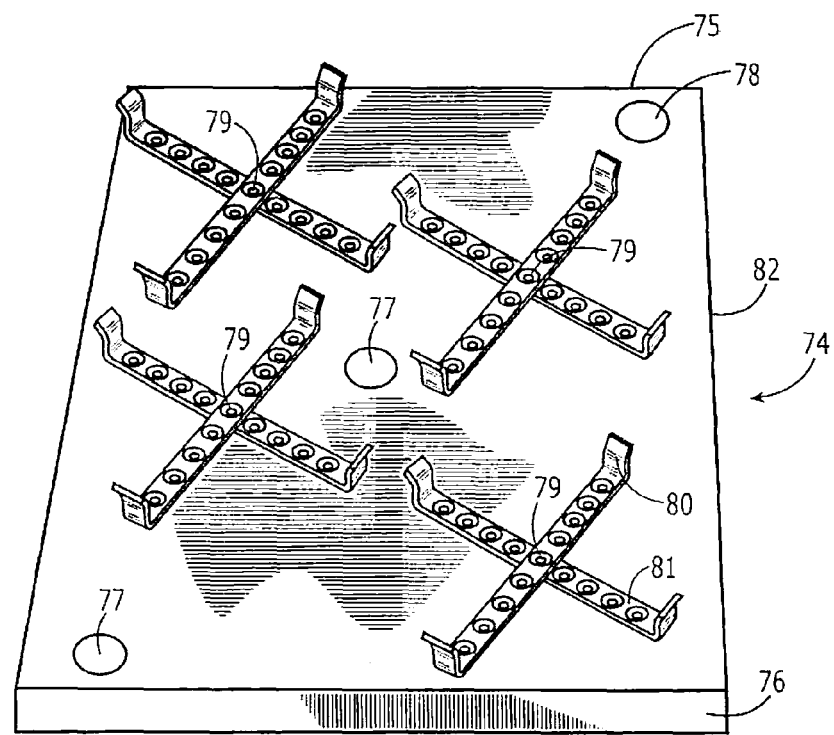

Yet another embodiment 70 (FIGS. 13-24), believed at the time of filing to represent a preferred embodiment, comprises a reactor vessel having a smooth upper edge 75 on the lip 76, and two inlets 77 for filling the vessel 74 (FIG. 13). A drain 78 permits emptying the vessel 74.

The vessel 74 in this embodiment 70 is adapted to hold four ultrasonic head arrays 43 as described above within four reactor holders 79 positioned in spaced relation within the vessel 74. Each reactor holder 79 comprises an "X"-shaped element having upwardly extending clips 80 at the end of each arm 81, the clips 80 positioned to surround the periphery of each ultrasonic head array.

In this embodiment 70 the reaction holders 79 are affixed to the bottom 82 of the reactor vessel 74, for example, via a glue such as epoxy, although this is not intended as a limitation. The holders 79 are beneficial in elevating the reactor head arrays so that treatment fluid may circulated under the reactor, helping to cool the head array. The holders 79 also permit a secure fit and easy removal of the head arrays for replacement or repair.

Figure 14:
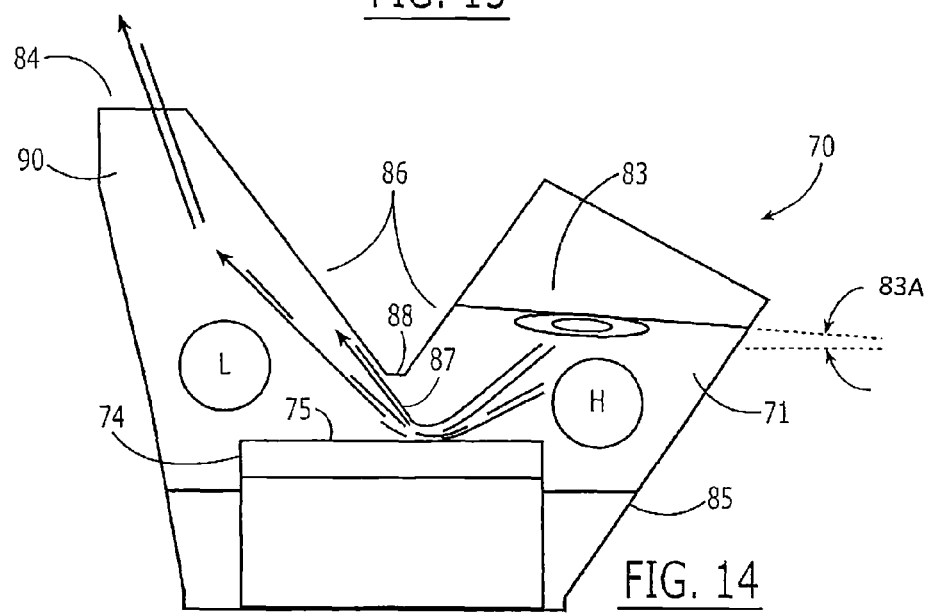

The cross-sectional view of FIG. 14 illustrates airflow (shown as double arrows) for this embodiment 70. An inlet fan 83 at a rear end of the tank 71 blows air toward the reactor vessel 74, and thence out the exhaust 84 at the front end of the tank 71, carrying along with it the particles created by the ultrasonic head arrays. The fluid level 85 is shown surrounding the vessel 74.

In a particular embodiment, the inlet fan 83 is mounted at an angle 83A of approximately 10 degrees to the horizontal. The shape of the tank 71 includes a substantially "V"-shaped compression region 86 leaving a gap 87 between the notch 88 of the "V" 88 and the top 75 of the vessel 74.

Figure 15:
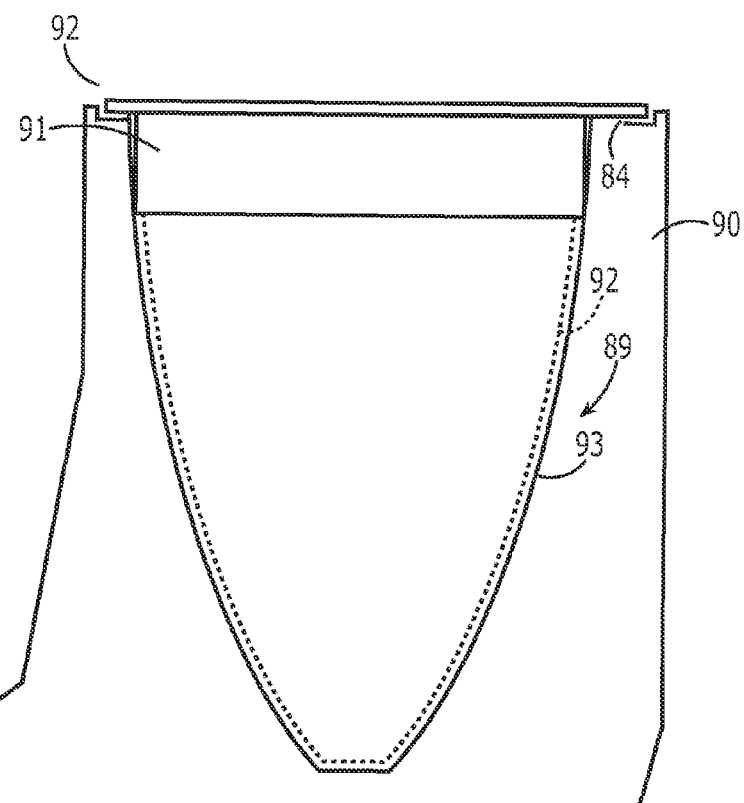
FIG. 15 is a side cross-sectional view of a particle filter in position within the chimney bore.
Figure 16A:
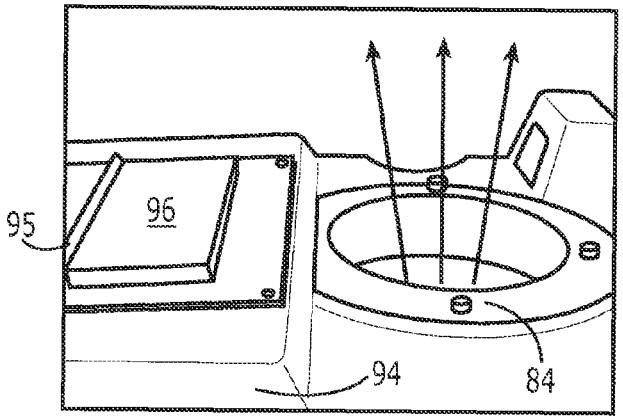
FIG. 16 is a side perspective view of the mass blower operation.
Figure 16B:
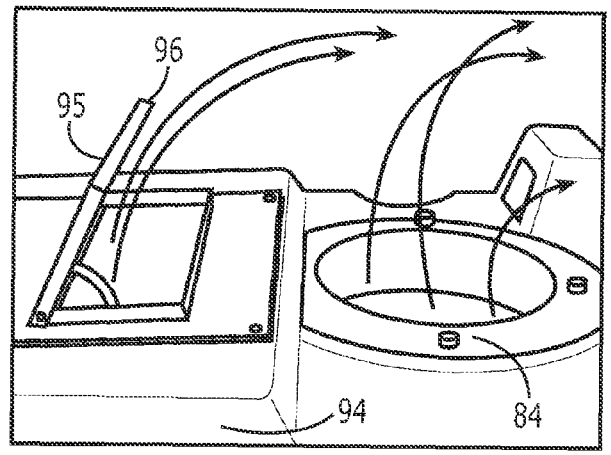
Figure 17:
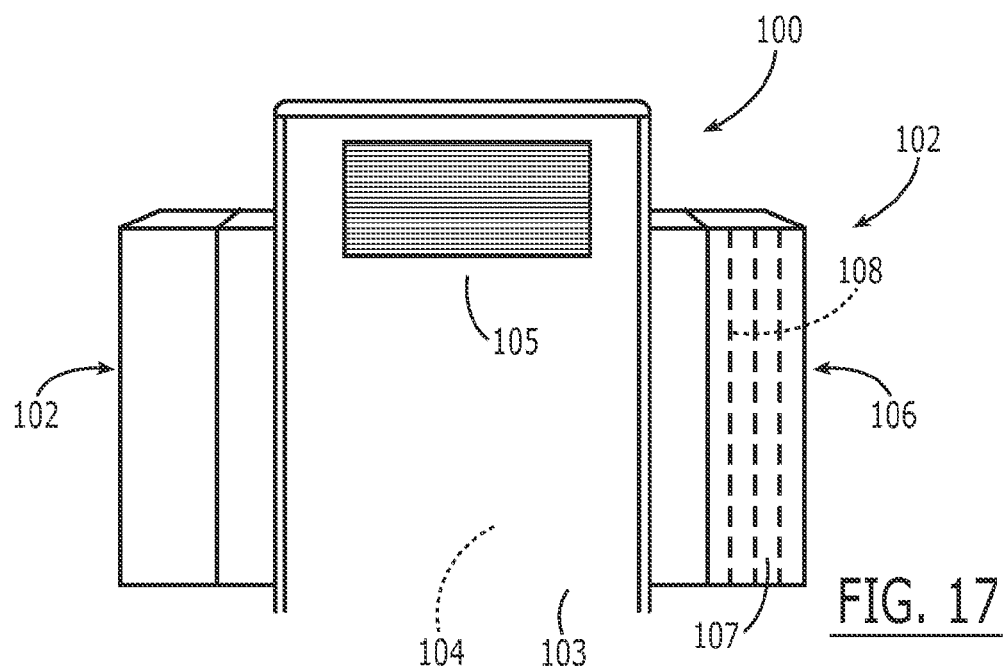
FIG. 17 is a front view of the scrubbing device of the present invention.

This device 70 further comprises a particle filter 89 positioned within the chimney bore 90 (FIG. 15). The particle filter 89 comprises a substantially inverted cone-shaped element having a substantially cylindrical support base 91 having an upper lip 92 for supporting the filter 89 within the chimney bore 90 at the exhaust aperture 84. The filter 89 further comprises a screen layer 92 surrounded by a mesh layer 93. In a particular embodiment, the screen layer 92 comprises a ½-in. plastic screen, and the mesh layer 93 comprises a ⅛-in. plastic mesh. The particle filter 89 prevents larger particles from being blown out the exhaust aperture 84, and fluid formed by filtered particles runs back into the tank 71. The particle filter 89 ensures that particles no greater than 5 μm are exhausted from the device 70, and are typically in a range of 0.25-5 μm.

The device 70 additionally comprises an outer shell 94 that encases the inner tank 71 of FIG. 14. The outer shell 94 comprises a mass blower 95 for generating air flow toward the exhaust aperture 84 for accelerating particles exiting therefrom, spreading the particles out and thereby providing faster introduction of the particles into the space to be treated (FIGS. 16A and 16B). The mass blower 95 has a door 96 that is movable between a closed position (FIG. 16A), wherein the particles exit substantially vertically, and an open position (FIG. 16B) wherein the particles are blown forward. Air flow generated via an inlet thus also creates a vacuum over the leading edge of the exhaust, helping to pull particles out of the chimney bore 90. When a fan for the mass blower 95 is turned on, the air pressure generated thereby opens the diverter door 96.

Yet a further feature of this embodiment 70 is a microparticle evacuation device 100 for scrubbing air in the treated space to remove any remaining particles, and also for creating an additional air current within the space to assist particles to attach to surfaces within the space (FIG. 17). This device 100 reduces the time required for reoccupation of the treated space, and is operated for a sufficient time to scrub the air three to four times, typically at a rate of 3000-3400 $ft^3$/min. A deodorizer can also be added in the airflow of the scrubber if desired.

The scrubbing device 100 is connectable to the treatment device 70, and uses 120 Vdc in a particular embodiment. The scrubbing device 100 can be operated via, for example, a touch screen. The scrubbing device 100 can also be operated independent of the treatment device 70, in a "manual" mode. The device 100 comprises a pair of series of air filters 102 positioned on a base 103 in opposed relation, each leading to an inner space 104 from which filtered air is expelled through an exhaust 105. Each of the series of air filters 102 can comprise, for example, a ¾-in. metal mesh 106 upstream of a 1¾ HEPA-style filter 107, which in turn is upstream of a 4-in. mini-pleat (95%) filter 108.

Figure 18:
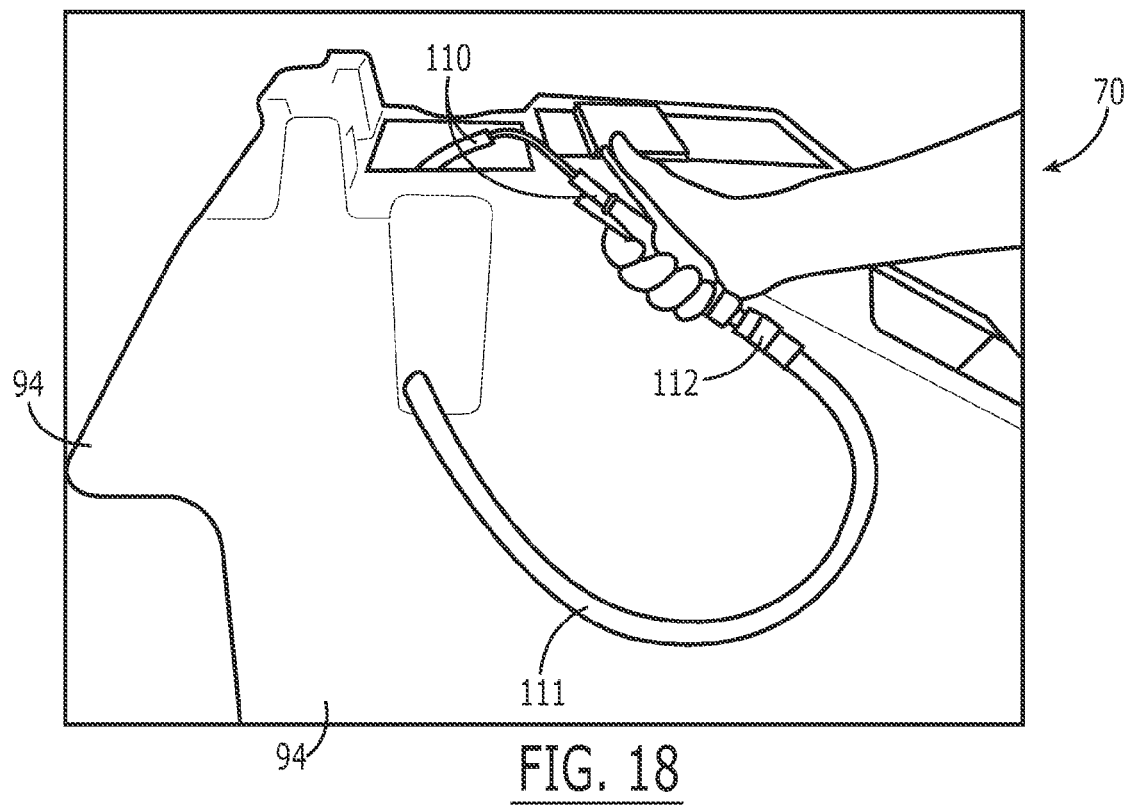
FIG. 18 illustrates the spray nozzle connection.

The "plumbing" aspect of the device 70 includes additional spray and fluid discharge features. The fluid, for example, can be administered directly (i.e., not in particulate form as generated by the ultrasonic head arrays) by way of a spray attachment 110 connectable to a hose 111 in fluid communication with the inner tank 71 (FIG. 18). The spray attachment 110 can be connectable to the hose 111, for example, a quick disconnect, and the hose 111 is retractable within the outer shell 94. The quick disconnect has a safety foot valve that is operator controlled to prevent fluid discharge when disconnected.

Figure 19:
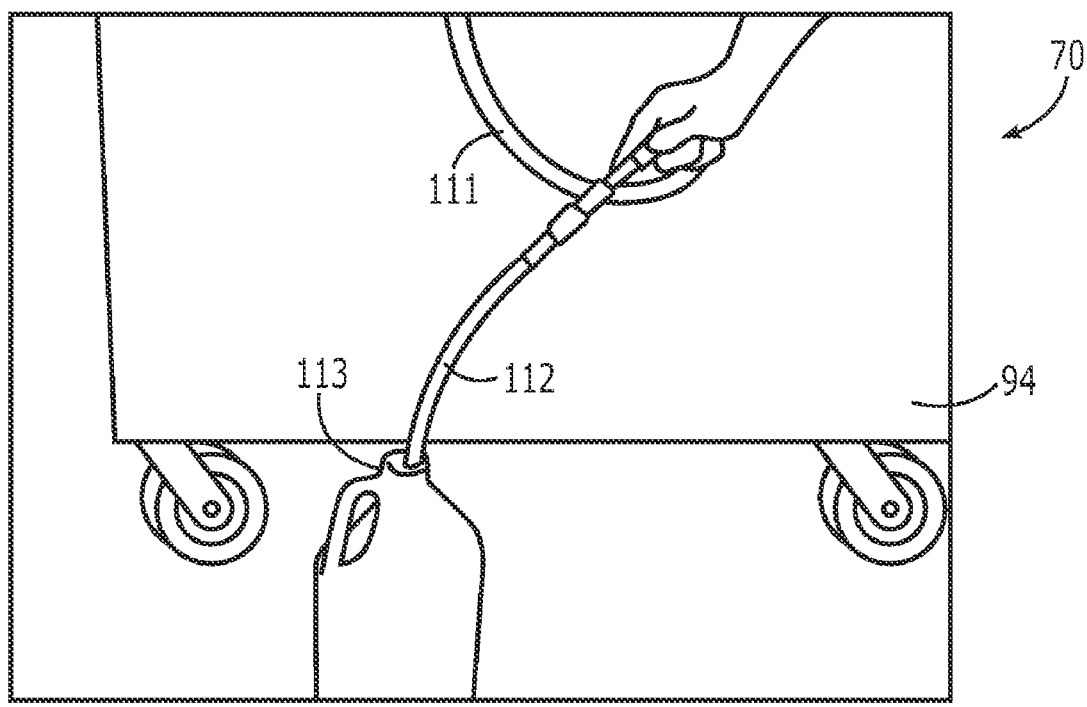
FIG. 19 illustrates the use of a discharge hose to empty the tank of fluid.
Figure 20:
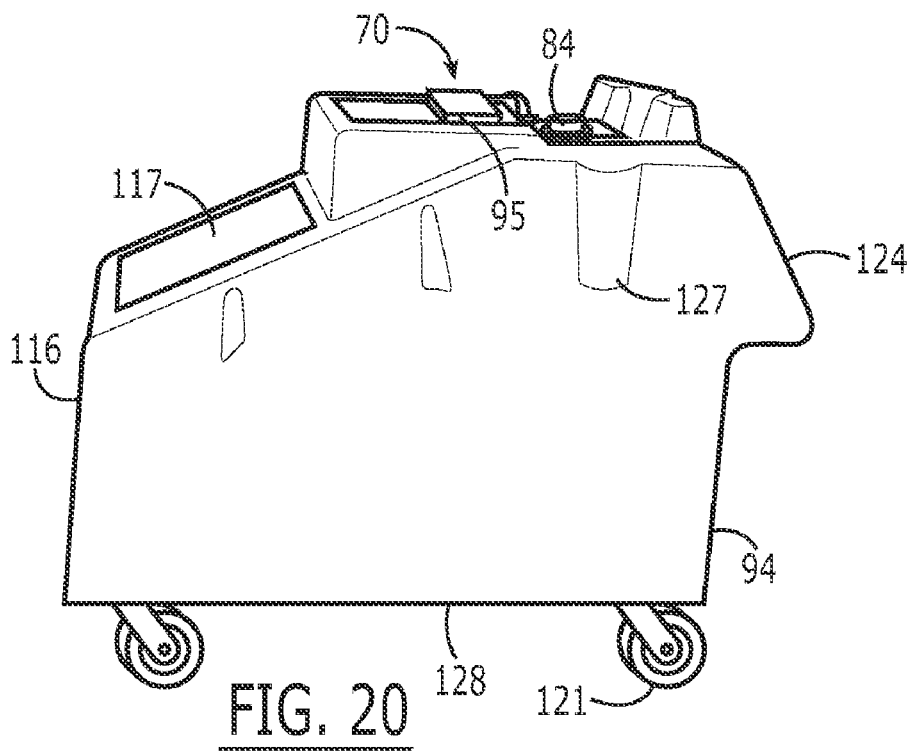
FIG. 20 is a side view of an embodiment of the device.
Figure 21:
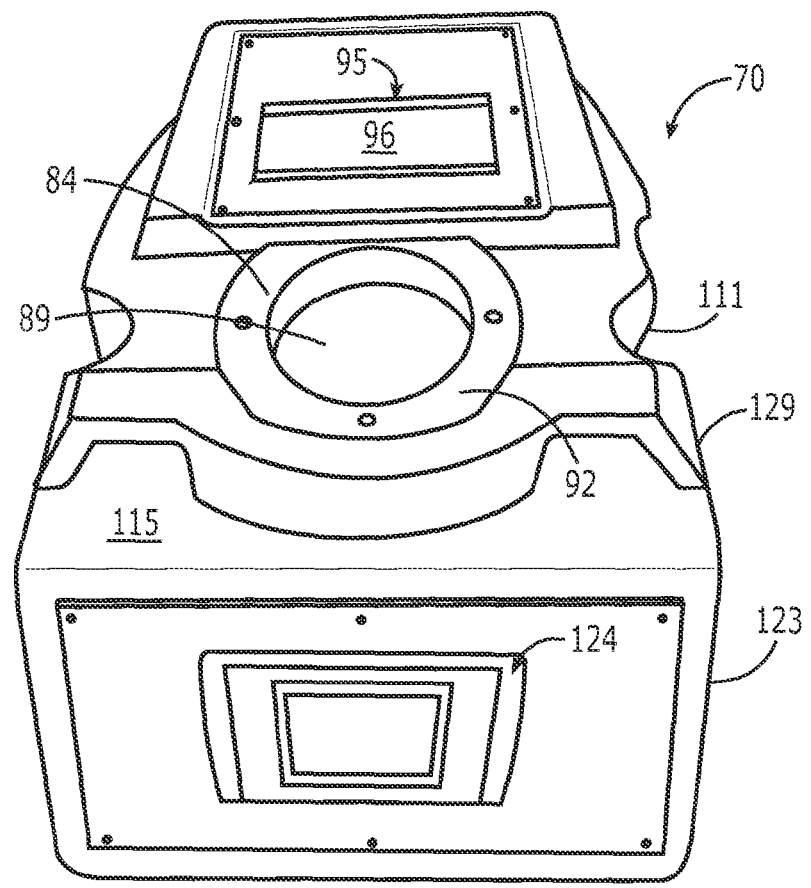
FIG. 21 is a front/side view of the device of FIG. 20.

The hose 111 can also be used to empty the tank 71 when the device 70 is not in use (FIG. 19). For this operation, a discharge hose sector 112 is connected to the hose 111, and the sprayer pump is used to discharge fluid for storage into, for example, a bottle 113 or other container.

The entire outer shell 94 and external components of this embodiment 70 are depicted in FIGS. 20-24, although these details are not intended to be limiting. The treatment exhaust 84 and mass blower 95 are positioned on the top 115 of the device 70, with the air inlets 116,117 to the mass blower 95 and the inner tank 71 on the front 118 and slanted upper faces 119, respectively. Handles 120 are provided, as well as wheels 121 for ease of movement. A controller 122 is positioned on the rear 123 of the device 70, along with a touch screen 124, power cord 125, and plug 126. The scrubber attachment 127 is on one side 128, and the sprayer hose 111 on the other side 129.

Figure 22:
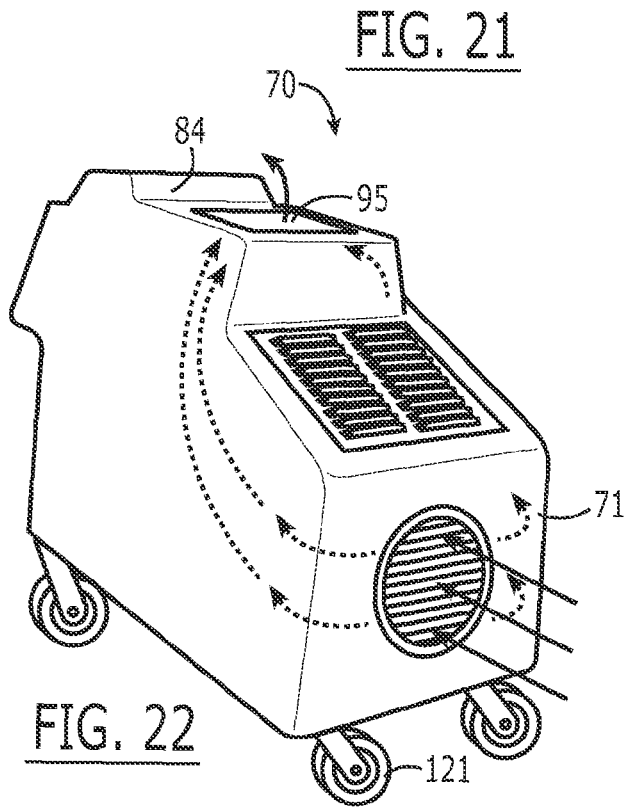
FIG. 22 is a top/rear view of the device of FIG. 20.
Figure 23:
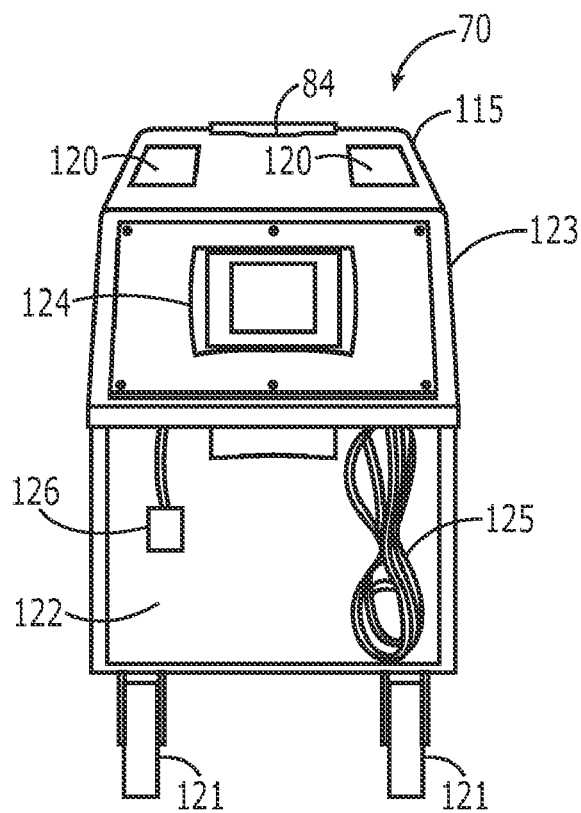
FIG. 23 is a rear view of the device of FIG. 20.
Figure 24:
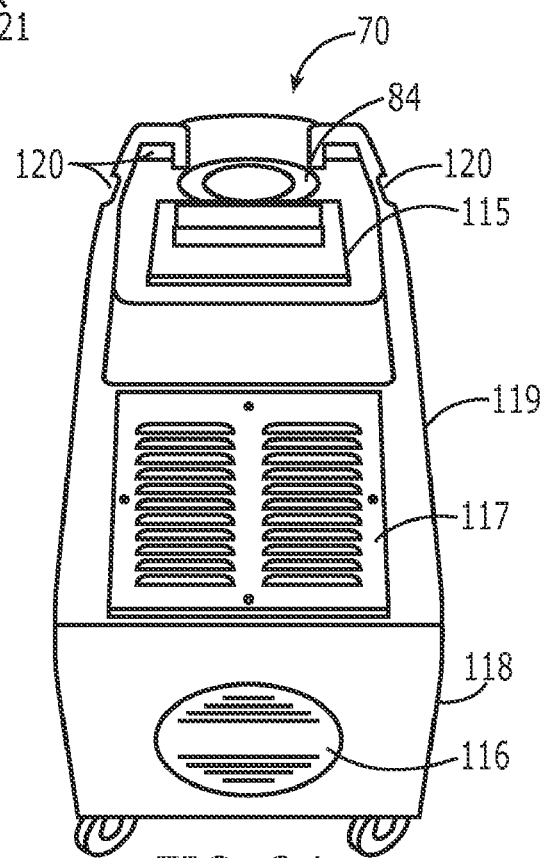
FIG. 24 is a top/front view of the device of FIG. 20.

An outline of the inner tank 71 is shown on FIG. 22, along with the air flows to the mass blower 95 and into the inner tank 71.

Figure 25:
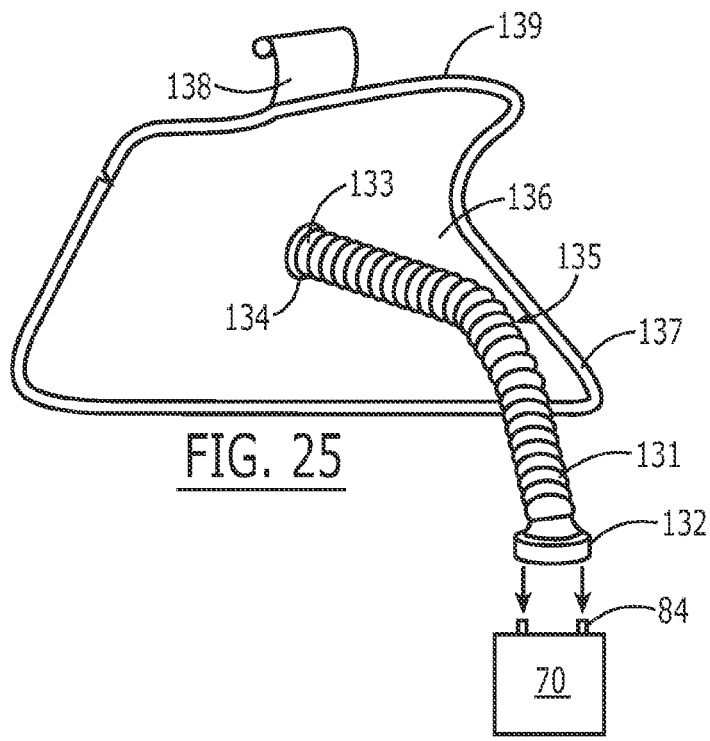
FIG. 25 is a front perspective view of a device for sanitizing a vehicle.
Figure 26:
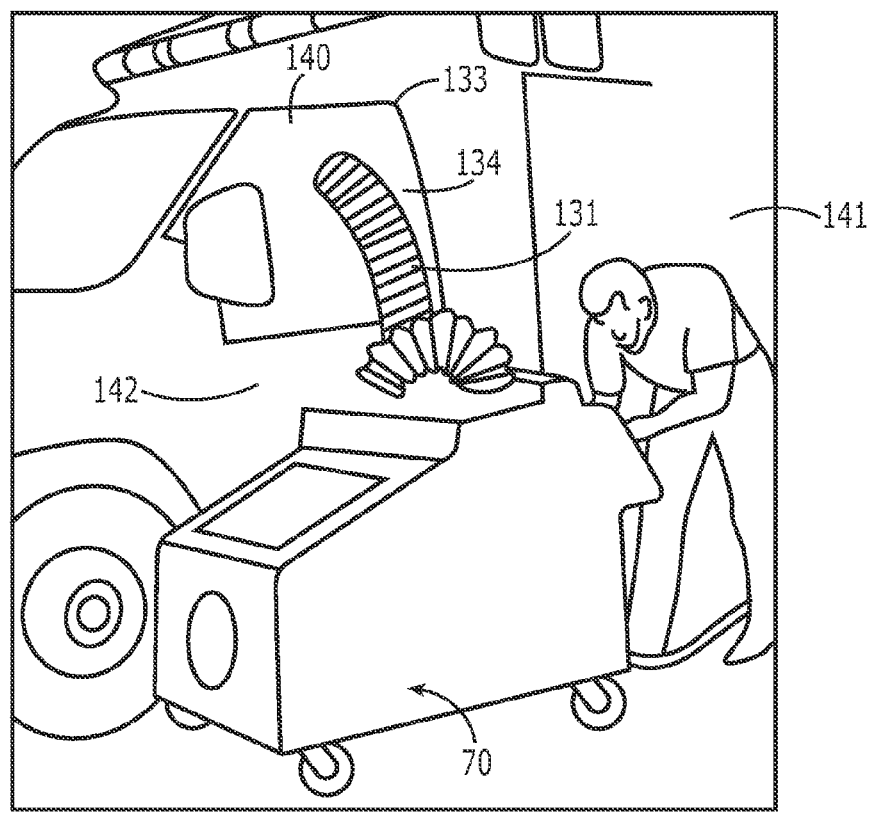
FIG. 26 is a side perspective view of the device of FIG. 25 in use.

Another aspect of the present invention is directed to a system 130 and method for sanitizing vehicle interiors (FIGS. 25 and 26). The system includes the device 70 as outlined above, and further comprises a hose 131 having a proximal end 132 that is affixable in fluid communication with the exhaust outlet 84. The distal end 133 of the hose 131 is affixable to an aperture 134 in a window seal element 135. In a particular embodiment, the window seal element 135 comprises a flexible, substantially planar overlay 136 having a magnetic seal edge 137 around the perimeter of the overlay 136. In a particular embodiment, the overlay 136 can comprise a vinyl material, although this is not intended as a limitation. Also in a particular embodiment, the hose 131 comprises a serpentine, 6-in.-diameter hose that can extend between 6 and 12 feet to enable its use in virtually any size vehicle. A top retaining tab 138 extends from a top edge 139 of the overlay 136, and the aperture 134 is positioned centrally in the overlay 136.

In use, a window 140 of a vehicle 141 is at least partially rolled down, and the vehicle door 142 is opened. The top retaining tab 138 is placed over the top of the door 142, and the window seal element 135 drapes down over the window 140. The door 142 is closed, and the magnetic seal edge 137 is pressed against the exterior of the door 142.

Next the hose 131 is attached to the fogging unit's exhaust 84, and the unit 70 is activated for a sufficient time to sanitize the vehicle's interior.

Another important feature of the present invention includes the liquid composition used for sanitizing spaces, and a method of making this composition. The invention is not intended to be limited, however, to the precise composition and proportion of ingredients in the liquid.

In a preferred embodiment, the composition is made as follows: 40 gallons of clean, carbon-filtered water is added to a clean plastic or stainless steel vessel, and a mixer is turned on. 1 pound of sodium metasilicate pentahydrate is mixed into the water slowly, and mixing continues for 5 min. With the mixer still running, a clean plastic pail is used to remove 1 gal of mixed solution for use in a pre-blending step. 70 ml of SE25 (Wacker Chemie AG, Munich, Germany), a silicone-based antifoaming agent, is added to the pail, and mixed using a clean plastic rod until the solution is blended thoroughly. At this point the solution will appear to be a cloudy micro-emulsion. 60 ml of K-2 surfactant (Lonza Chemical Corporation, Switzerland), used as a molecular coupler, is mixed slowly into the micro-emulsion until thoroughly blended.

With the mixer running, the pre-blend is added back into the first vessel at a rate of 180 ml per min while the mixer is running, and the mixer continues to run after the pre-blend has been added. Into a clean 1000-ml beaker containing 700 ml distilled water, 2 oz of Palaklor-1103041 (Pylam Products Company, Inc., Tempe, Ariz.) is added. This substance comprises a dye base for its ultraviolet reflective traits and can be used as tracer. The Palaklor is not necessary for the sanitizing aspect of the inventive composition, and can therefore be omitted if a tracer is not desired in the mixture. The mixture is shaken for 1 min, and is then added to the first vessel with continued mixing.

Water is added to the first vessel to bring the volume up to 55 gal, and mixing continues for 15 min. When blending is complete, the mixture stands for 1 h prior to packaging. For use, the mixture is diluted 1:1 with water.

To the mixture may be added sanitizing, disinfectant, and/or insecticidal elements such as, but not intended to be limited to, di-N-alkyl($C_{8-10}$)-N,N-dimethylammonium chloride, N-alkyl($C_{10-12}$)dimethylammonium chloride, tetrasodium ethylenediamine tetraacetate, sodium ethanol, 2-propanol, pyrethrum, octylphenoxypolyethoxyethanol (a nonionic surfactant), quaternary ammonia, formaldehyde, and peroxide.

The composition has been shown to kill pathogens of hepatitis B and C, *staphylococcus aureus, streptococcus,* avian influenza, tuberculosis, *enterococcus* bacteria, HIV, *E. coli, pseudomonas, salmonella, listeria,* Legionnaire's disease, human coronavirus, toxic molds, fecal coliform, and athlete's foot, among others.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus and composition illustrated and described herein are by way of example, and the scope of the invention is not limited to the exact details of construction, constituents, and proportion.

What is claimed is:

1. A method for sanitizing a space, the method comprising the steps of:
    providing a tank having a compression area within an interior space of the tank between an inlet and an outlet thereof:
    placing a reactor vessel within the compression area, the reactor vessel having an ultrasonically vibratable disc at a fixed location within the reactor vessel and below a top edge thereof;

placing an aqueous sanitizing liquid into the interior space of the tank;

transferring liquid from the tank interior space into the reactor vessel so as to fill the reactor vessel to the top edge thereof, the reactor vessel supported within the tank interior space and above a bottom of the tank;

continuously transferring the liquid into the reactor vessel for causing the liquid to continuously cascade over the top edge thus maintaining a fixed depth of the ultrasonically vibratable disc below a surface of the liquid;

vibrating the ultrasonically vibratable disc to form an atomized fog of a plurality of particles emitted from the aqueous sanitizing liquid;

providing a preselected flow of air within the interior space from the inlet toward the outlet of the tank, the air flowing through the compression area from a high pressure to a lower pressure, and causing smaller particles within the plurality of particles to move more quickly toward the outlet than larger particles thereof, the preselected flow of air allowing at least a portion of the larger particles to fall back to the bottom of the tank;

placing an overlay having an aperture therein onto an opening to an interior space of a vehicle sufficient for sealing the opening;

connecting a conduit between the outlet of the tank and the aperture of the overlay sealing the interior space of the vehicle; and exhausting the smaller particles within the plurality of particles formed in the atomized fog from the outlet into the interior space of a vehicle.

2. The method recited in claim 1, further comprising the steps of sealing an at least partially open access area of a vehicle and channeling the formed atomized fog resulting from the exhausting step into an interior of the vehicle for enabling a sanitizing treatment of the interior of the vehicle.

3. The method recited in claim 2, further comprising the step of scrubbing air within the interior of the vehicle of the atomized fog therein by a filtering thereof following the channeling step.

4. The method recited in claim 1, wherein the opening comprises an open window.

5. The method recited in claim 1, wherein the overlay comprises a generally planar overlay having magnets extending about a periphery thereof, and wherein the placing step comprises magnetically attaching the overlay onto the vehicle.

6. A method for sanitizing a space, the method comprising the steps of:

providing a tank having a compression area within an interior portion of the tank between an inlet and an outlet thereof, wherein the air flow moves from a high pressure area to a low pressure area, the compression area thus increasing speed of flow toward the outlet;

placing a reactor vessel within the compression area, the reactor vessel having an ultrasonically vibratable disc fixed within the reactor vessel and below a top edge thereof;

placing an aqueous sanitizing liquid into the interior portion of the tank;

transferring liquid from the tank interior portion into the reactor vessel so as to fill the reactor vessel to the top edge thereof, the reactor vessel supported within the tank interior portion such that the top edge of the reactor vessel is above the liquid within the interior portion of the tank;

continuously transferring the liquid into the reactor vessel for causing the liquid to continuously cascade over the top edge, thus maintaining a fixed depth of the ultrasonically vibratable disc below a surface of the sanitizing liquid;

vibrating the ultrasonically vibratable disc to form a plurality of particles emitted from the aqueous sanitizing liquid, the plurality of particles ranging in size;

providing a preselected flow of air within the interior space from the inlet toward the outlet of the tank, the air flowing through the compression area thus causing smaller particles within the plurality of particles to move more quickly toward the outlet than larger particles within the plurality of particles thereof, the preselected flow of air allowing at least a portion of the larger particles to fall back to the bottom of the tank;

filtering a substantial portion of the plurality of particles through a particle filter comprising an inverted cone-shape having a top end proximate the outlet, the filter collecting the larger particles and allowing the larger particles to drop to the bottom of the tank, and permitting the smaller particles to pass therethrough;

placing an overlay having an aperture therein onto an opening to an interior space of a vehicle sufficient for sealing the opening;

connecting a conduit between the outlet of the tank and the aperture of the overlay sealing the interior space of the vehicle; and exhausting the filtered smaller particles from the outlet to the interior space of a vehicle for a sanitizing thereof.

7. The method recited in claim 6, further comprising sealing an at least partially open access area of a vehicle and channeling the filtered smaller particles into an interior of the vehicle for enabling a sanitizing treatment thereof.

8. The method recited in claim 7, further comprising scrubbing air within the interior space of the vehicle of remaining particles following a treatment of the interior space.

9. The method recited in claim 6, wherein the opening comprises an open window.

10. The method recited in claim 6, wherein the overlay comprises a generally planar overlay having magnets extending about a periphery thereof, and wherein the placing step comprises magnetically attaching the overlay onto the vehicle.

* * * * *